United States Patent
Schindler et al.

(10) Patent No.: US 10,588,546 B2
(45) Date of Patent: Mar. 17, 2020

(54) SYSTEMS AND METHODS TO ASSESS BALANCE

(71) Applicant: THE CLEVELAND CLINIC FOUNDATION, Cleveland, OH (US)

(72) Inventors: David D. Schindler, Russell, OH (US); Jay L. Alberts, Chagrin Falls, OH (US); Joshua R. Hirsch, Brecksville, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 745 days.

(21) Appl. No.: 14/316,217

(22) Filed: Jun. 26, 2014

(65) Prior Publication Data
US 2015/0005674 A1    Jan. 1, 2015

Related U.S. Application Data

(60) Provisional application No. 61/839,634, filed on Jun. 26, 2013.

(51) Int. Cl.
| | | |
|---|---|---|
| *A61B 5/11* | (2006.01) | |
| *A61B 5/00* | (2006.01) | |
| *G16H 50/50* | (2018.01) | |
| *G16H 50/30* | (2018.01) | |
| *G16H 50/20* | (2018.01) | |
| *G16H 50/70* | (2018.01) | |

(52) U.S. Cl.
CPC .......... *A61B 5/1121* (2013.01); *A61B 5/1117* (2013.01); *A61B 5/4082* (2013.01);
(Continued)

(58) Field of Classification Search
CPC .............................. A61B 5/1117; A61B 5/1121
See application file for complete search history.

(56) References Cited

U.S. PATENT DOCUMENTS

| | | |
|---|---|---|
| 6,774,885 B1 | 8/2004 | Even-Zohar |
| 6,997,882 B1 | 2/2006 | Parker et al. |
| | (Continued) | |

FOREIGN PATENT DOCUMENTS

| | | |
|---|---|---|
| WO | 2010073044 A1 | 7/2010 |
| WO | 2013054257 A1 | 4/2013 |

OTHER PUBLICATIONS

Balance System SD, "Balance Assessment & Conditioning", Biodex Medical Systems, Inc., New York, Biodex.com/balance, pp. 1-6.
(Continued)

*Primary Examiner* — Daniel L Cerioni
*Assistant Examiner* — Yasmeen S Warsi
(74) *Attorney, Agent, or Firm* — Tarolli, Sundheim, Covell & Tummino LLP

(57) ABSTRACT

This disclosure relates to a system and method to analyze balance and stability of a patient. Test data for the patient, representing motion of a device affixed to the patient during a test interval (e.g., at a position approximating the center of mass, such as in proximity to the torso), can be received. The test data can be processed to provide processed data (or sensor-derived data) that includes at least one of acceleration data, rotational rate data and rotational position data for the test interval. A biomechanical model can be applied to the processed data to provide center of mass (COM) motion data representing movement of the COM in multiple dimensions for the patient during the test interval. An indication of balance for the patient can be determined based on the COM motion data. The indication of balance can be used to analyze the balance and stability of the patient.

12 Claims, 14 Drawing Sheets

(52) U.S. Cl.
CPC ........... *A61B 5/6898* (2013.01); *G16H 50/20* (2018.01); *G16H 50/30* (2018.01); *G16H 50/50* (2018.01); *G16H 50/70* (2018.01)

(56) References Cited

U.S. PATENT DOCUMENTS

| | | |
|---|---|---|
| 7,931,604 B2 | 4/2011 | Even Zhoar et al. |
| 8,079,251 B2 | 12/2011 | Miyanaga |
| 2010/0131113 A1 | 5/2010 | Even-Zhoar |
| 2010/0277489 A1* | 11/2010 | Geisner ................ G06F 3/011 345/581 |
| 2011/0208444 A1 | 8/2011 | Solinsky |
| 2012/0253201 A1* | 10/2012 | Reinhold .............. A61B 5/1113 600/473 |
| 2012/0253233 A1 | 10/2012 | Greene et al. |
| 2013/0035613 A1 | 2/2013 | Curtiss |

OTHER PUBLICATIONS

Biodex, "Addendum Biodex Balance SD Software Upgrade Version 1.32 Release Notes", Biodex Medical Systems, Inc., pp. 1-24.
Geijtenbeek et al., "D-Flow: Immersive Virtual Reality and Real-Time Feedback for Rehabilitation", pp. 1-8.
Roetenberg "Inertial and Magnetic Sensing of Human Motion", May 2006, pp. 1-128.
PCT International Search Report and Written Opinion for PCT/US2014/044388, dated Nov. 28, 2014, pp. 1-14.

* cited by examiner

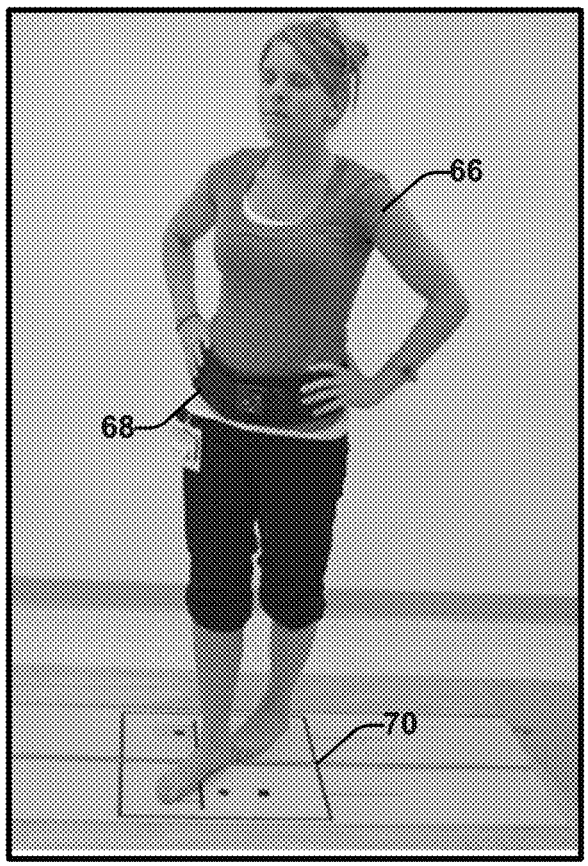 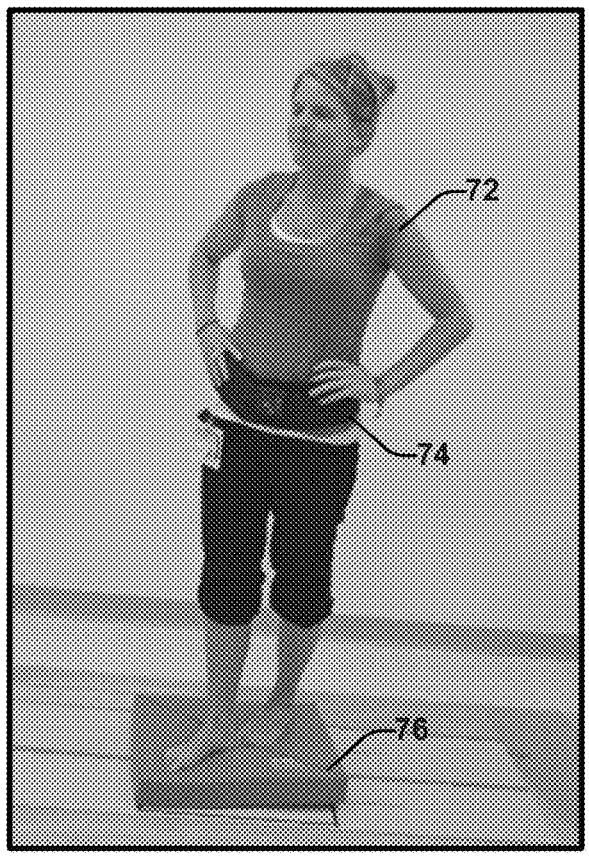
FIG. 6A  FIG. 6B

SYSTEMS AND METHODS TO ASSESS BALANCE

RELATED APPLICATIONS

This application claims the benefit of U.S. Provisional Patent Application Ser. No. 61/839,634, filed Jun. 26, 2013, entitled "SYSTEM AND METHOD TO ASSESS BALANCE AND STABILITY." This provisional application is hereby incorporated by reference in its entirety.

GOVERNMENT FUNDING

This invention was made was government support under NS073717 awarded by the National Institutes of Health. The government has certain rights in this invention.

TECHNICAL FIELD

This disclosure relates generally to balance, and more specifically to systems and methods to assess balance of a patient.

BACKGROUND

Generally, balance is the ability to maintain the line of gravity of a body within the base of support with minimal postural sway. Sway is the horizontal movement of the centre of gravity or mass, which can occur in the anterior-posterior or medial-lateral directions. A person's balance can be impaired due to conditions, such as aging, concussion, stroke, spinal cord injury, Parkinson's disease, multiple sclerosis, or the like. Currently, center of pressure measured from a force plate is considered the gold standard measure of balance. However, force plates and associated measurement systems tend to be quite large, non-portable, and expensive.

SUMMARY

This disclosure relates to systems and methods to assess balance of a patient.

In an example, a computer-implemented method is described. Test data for a patient that represents motion of a portable (e.g., mobile) device affixed to the patient during a test interval can be received. The test data can be processed to provide processed data that includes acceleration data, rotational rate data and rotational position data for the test interval. A biomechanical model can be applied to the processed data to provide center of mass (COM) motion data representing movement of the COM in multiple dimensions for the patient during the test interval. An indication of balance for the patient can be determined based on the COM motion data.

In another example, a non-transitory computer-readable medium is described that stores instructions executable by one or more processors to perform operations. A test data interface can receive test data for a patient that represents motion of a set of sensors attached to a patient's torso to approximate the patient's center of mass during a test interval. A test data calculator can process the test data to provide sensor-derived data that includes acceleration data, rotational rate data and rotational position data for the test interval. A center of mass (COM) calculator can apply a biomechanical model to the processed data to provide COM motion data representing movement of the COM in multiple dimensions for the patient during the test interval. A balance analyzer can determine an indication of balance for the patient based on the COM motion data.

BRIEF DESCRIPTION OF THE DRAWINGS

FIGS. 6A and 6B depict examples of images showing a patient performing yet another test that can be used to assess balance of a patient with a portable data capture device attached to the patient.

DETAILED DESCRIPTION

Figure 1:
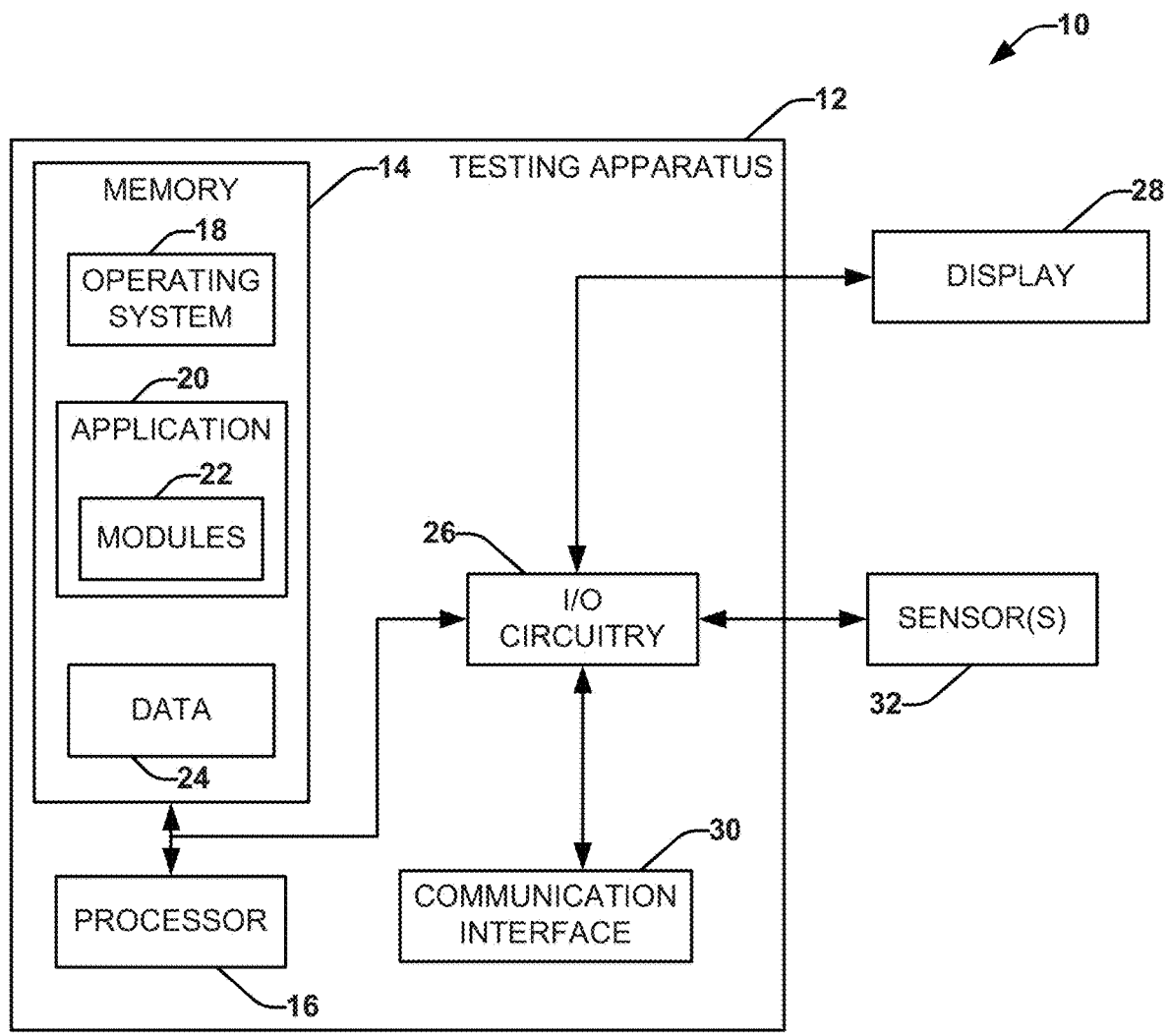
FIG. 1 depicts an example of a block diagram of a system that can be used to assess balance of a patient.

This disclosure relates to a system and method that can be used to analyze balance (and/or stability) of a patient and/or healthy person (e.g., an adult and/or a child). For example, the analysis of balance and can be used in connection with diagnosing and/or tracking progression of a neurological or neuromotor condition (e.g., concussion, stroke, multiple sclerosis, Parkinson's disease, or the like). Additionally or alternatively, the analysis of balance can be used in the evaluation of the effectiveness of a behavioral, pharmacological, and/or surgical procedure. As another example, the system can be employed in the assessment of balance (e.g., in inpatient and/or outpatient settings) to determine a fall risk (e.g., a computed value indicative of a risk that an individual might fall down) The analysis can be based on test data acquired by one or more sensors during a test interval of a static or dynamic balance test (e.g., a single leg test, a double leg test, a tandem leg test, a single leg test on pad, a double leg test on pad, a tandem leg test on pad, and/or tandem gait test). The test interval can be the time between the start and the finish of a balance test.

The sensors can be configured to acquire the test data in multiple dimensions over the test interval. For example, the sensors can include one or more motion sensors and/or one or more inertial sensors (e.g., an accelerometer, a gyrometer, a magnetometer, a tilt sensor or a proximity sensor). The test data can include displacement data (e.g., linear displacement data, rotational displacement data, etc.). For example, the sensors can be integrated within and/or connected to a portable device (e.g., a mobile phone, tablet computer or a special-purpose device). The portable device can be attached to a predetermined location on a patient's torso to approximate a center of gravity of the patient (e.g., overlying the patient's lower back or abdomen) to facilitate conversion of the test data from the sensors in the portable device to the patient's center of mass (COM) so that the test data corresponds to motion and/or inertia of the patient's COM.

By way of example, the test data can be processed to determine processed data (e.g., sensor-derived data, including velocity data, acceleration data, jerk data, rotational rate data, rotational position data, etc.) for the test interval. A biomechanical model can be applied to the processed data to provide COM motion data representing movement of the COM in multiple dimensions for the patient during the test interval. An indication of balance for the patient can be determined based on the COM motion data. The COM motion data can be determined for each test (and/or each test interval) completed by the patient. Additional data can be determined based on comparative evaluations or statistical evaluations based on the COM motion data computed for each test.

Analysis of the balance and/or stability can be accomplished based on the COM motion data. For example, an output can be constructed based on the COM motion data and configured to be displayed on a display. The output can be a visualization that can be animated in real time during the tests or generated based on stored data from a prior test. The visualization can present an avatar (e.g., in one or more different views, including a top view, a side view, a front view, etc.) of a person. For example, the avatar can demonstrated patient's movement (e.g., along the anterior-posterior direction and/or the medial-lateral direction), which can be animated in three dimensions based on the sensor data, the processed sensor data, and/or the COM motion data so that a user can visually see how the patient's balance motion compares to one or more baseline data corresponding to one or more "normal" subjects that represents a normal balance for a patients of similar age, health status, gender, physical fitness, height, weight, etc.

In some examples, the 3D animation of the patient can be superimposed on a baseline reference that has been established by a healthy patient, which can be the same patient (e.g., from baseline data) or a hypothetical statistically normal patient (e.g., based on baseline data from one or more "normal" patients with characteristics similar to the patient). Additionally or alternatively, the animation can include a balance motion reference that has been established from the current patient's balanced motion data, and a plumb reference (which is directed toward the patient's distribution of weight).

Additionally or alternatively, the output can include a plot of the motion of the COM based on the COM motion data. For example, the COM motion data can also be utilized to compute an area and/or a volume that can be compared to an area and/or a volume from a reference for the patient or other known baseline. The comparison allows the user to visually determine how much the patient is deviating from the reference. Furthermore, a score can be calculated based on (or as a function of) the determined COM area (see, e.g., FIGS. 9-11) and/or COM volume (see, e.g., FIG. 12). As another example, a score can be computed based on a comparison between the patient's COM area relative to a baseline area to provide an indication of the patient's balance or neuromotor function. Additionally or alternatively, a score can be calculated based on the computed COM volume or based on a comparison between the patient's COM volume relative to a baseline volume to provide an indication of the patient's balance or neuromotor function. As an example, one or more of the computed the score(s) and/or the visualizations can be utilized as part of a screening process for evaluating concussion related injuries, stroke, multiple sclerosis, Parkinson's disease as well as other neurological or neuromotor conditions.

FIG. 1 depicts an example of a system 10 configured to assess balance of a patient (or a plurality of patients). The system 10 can include at least a testing apparatus 12, a sensor 32 (or a set of one or more sensors), and a display 28. The sensor 32 and the display are each communicatively coupled to the testing apparatus 12 (e.g., via I/O circuitry 26). Although the sensor 32 and the display 28 are illustrated as separate from the testing apparatus, one or both of the sensor 32 and the display 28 can be integrated within the testing apparatus.

The testing apparatus 12 can include one or more computing apparatuses that can include a memory 14 and a processor 16. The memory 14 can be a non-transitory memory that can be configured store machine readable instructions and data 24. By way of example, the memory 14 can store a variety of machine readable instructions and data 24, including an operating system 18, one or more application programs 20, program modules 22 associated with the application, and data 24, including test data, program data, and/or other data. The operating system 18 can be any suitable operating system or combinations of operating systems, which can depend on manufacturer and system to system corresponding to different computer manufacturers.

The data 24 can include test data. The test data can be real time data acquired for an ongoing balance test (e.g., the data is buffered in random access memory) or the test data can be previously acquired data. The other data can include other types of motion data for a patient acquired during a test, image data acquired from one or more digital cameras (e.g., to show actual patient motion), demographic or personal information about the patient for which the other device data has been acquired. For example, the other data can be input into the testing apparatus 12 or can be acquired for the patient, such as from an electronic health record or other database that may contain information about the respective patient.

The memory 14 can be implemented, for example as volatile memory (e.g., RAM), nonvolatile memory (e.g., a hard disk, flash memory, a solid state drive or the like) or combination of both. It is to be understood that the memory 14 does not require a single fixed memory but the memory can include one or more non-transitory machine readable memory (e.g., volatile and/or non-volatile memory devices) that can store data and instructions. The memory 14 can store data 24 and/or instructions corresponding to the operating system 18 and/or the application in a single device or distributed across multiple devices, such as in a network or a cloud computing architecture.

The processor 16 can be configured to access the memory 14 and execute the machine readable instructions to facilitate the performance of operations (e.g., corresponding to the operating system 18 and/or the application programs 20). For example, the processor 16 can be configured to access the memory 14 to access the application programs 20 and the associated program modules 22 to implement the functions of the testing apparatus 12 with regard to the analysis of the patient's balance and/or postural stability. The application programs 20, associated program modules 22, and data 24 (including test data acquired by sensor 32) can cooperate to analyze the balance and/or stability of the patient based on computing an indication of balance of a patient, such as disclosed herein.

In some examples, the testing apparatus 12 can be implemented as a stationary personal computer or workstation. In other examples, the testing apparatus 12 can be implemented as a portable computer, such as a notebook computer, a tablet computer or smart phone. The testing apparatus 12 can include or communicatively coupled via I/O circuitry 26 and a communication interface 30 (which can be either internal to the testing apparatus 12 or external to the testing apparatus) to an input device (e.g., display 28 including a touchscreen) that provides a human-machine interface (HMI) that a user can employ to interact with the testing apparatus 12. As used herein, a user can refer to a person who uses the testing apparatus 12, such as a test administrator, a doctor, a nurse, a patient, a researcher, or the like. As used herein, a patient can refer to a living subject (e.g., adult or child) in need of treatment by a physician, physician assistant, advanced practice registered nurse, veterinarian, or other health care provider or the subject may be a healthy subject that is to be tested for other reasons.

For example, the communication interface 30 can include one or more network interfaces that are configured to provide for communication with a corresponding network, such as can include a local area network or a wide access network (WAN) (e.g., the internet or a private WAN) or a combination thereof. The communication interface can implement a wireless and/or physical communications technology for communicating with the network. As a further example, the communication interface 30 can send data 24 (e.g., test data and/or analysis data derived from test data) to a remote database. For instance, the testing apparatus 12 can be programmed upload and transfer such data to a remote database including an electronic health record (EHR) for the patient. Such transfer of data can be HIPPA compliant and provided over a secure tunnel (e.g., HTTPS or the like). The transfer of test data and/or analysis data can be automated to occur upon completion of one or more balance tests. The data 24 provided by the testing apparatus 12 can further be analyzed by an external analysis system.

The sensor 32 can be configured to acquire test data corresponding to movement of the COM of the patient during a test interval between the start and finish of a balance test. Examples of individual tests that can each include corresponding test data for respective intervals can include a single leg test, a double leg test, a tandem leg test, a single leg test on pad, a double leg test on pad, and/or a tandem leg test on pad. The sensor 32 can communicate the test data to the testing apparatus 12 to store in the memory 14 (e.g., as data 24). The stored test data can be timestamped during the test interval and programmatically associated with (e.g., tagged) each respective test or test sub-part during the test interval. The sensor 32 can be configured to acquire the test data in multiple dimensions over the test interval.

By way of example, the sensor 32 can include a motion sensor and/or an inertial sensor (e.g., an accelerometer, a gyrometer, a magnetometer, a tilt sensor and/or a proximity sensor) that can acquire data in two or three dimensions responsive to patient movement and interactions during the test interval. The test data can correspond to time series data acquired at a sample rate (e.g., 100 Hz) according to the sampling frequency of each respective sensor within sensor 32 for each test interval. The test data can include displacement data (e.g., linear displacement data, rotational displacement data, etc.). The sensor 32 can be fixed relative to the patient during the data acquisition process.

As an example, the sensor 32 can include one or more three-axis accelerometers. The one or more accelerometers can be configured to measure acceleration of the apparatus along one or more axis, such as to provide an indication of acceleration (e.g., an acceleration vector) of the apparatus in three dimensions. The one or more accelerometers can measure the static acceleration of gravity in tilt-sensing applications, as well as dynamic acceleration resulting from motion or shock. Additionally, the one or more accelerometers can possess a high resolution (4 mg/LSB) that can enables measurement of inclination changes less than 1.0°, for example. The one or more accelerometers may provide various sensing functions, such as activity and inactivity sensing to detect the presence or lack of motion and if the acceleration on any axis exceeds a user-defined level. The one or more accelerometers can also sense tapping (e.g., single and double taps) on a surface such as a touchscreen as well as sense free-fall if the device is falling. These and other sensing functions can provide output data. An example accelerometer is the ADXL345 digital accelerometer available from Analog devices. Other accelerometers could be utilized.

As another example, the sensor 32 can include a three-axis gyroscope that can be configured to sense orientation of the device along three orthogonal axes. The gyroscope can provide output data corresponding to orientation of the testing apparatus 12 along three orthogonal axes. The gyroscope can be implemented as 3-axis MEMS gyro IC, such as including three 16-bit analog-to-digital converters (ADCs) for digitizing the gyro outputs, a user-selectable internal low-pass filter bandwidth, and a Fast-Mode I$^2$C (400 kHz) interface. The gyroscope can also include an embedded temperature sensor and a 2% accurate internal oscillator. An example gyroscope that can be utilized is the ITG-3200 3 IC available from InvenSense, Inc. Other gyroscopes could be utilized. Additionally, both the three-axis gyroscope and the three-axis accelerometer can be utilized in combination.

The sensor 32 can be included within a portable device (e.g., a smart phone, a tablet computer or a special-purpose device). However, the sensor 32 need not be included within a portable device (e.g., a sensor array). Examples of the portable devices that can include integrated sensors (e.g., multi-axis accelerometers and gyroscopes) are shown in FIGS. 2-6.

Figure 2:
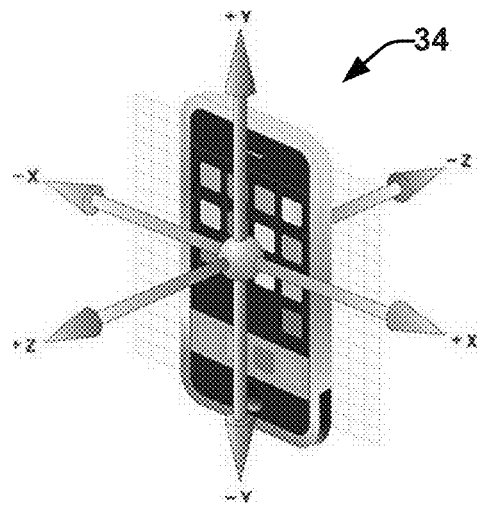
FIG. 2 depicts a schematic example of a portable data capture device that can be utilized in the assessment of balance of a patient.

FIG. 2 shows an example of a portable device 34 (e.g., a tablet computer or a smart phone) that can include the sensor 32 of FIG. 1. For example, the portable device 34 can include at least an accelerometer and a gyrometer that can be operable to detect motion and/or inertia in three dimensions (e.g., X, Y, and Z). The portable device 34 can be attached to a patient by an attachment mechanism (e.g., a belt, strap or harness) so that the test data can be processed to provide COM test data corresponding to motion and/or inertia of the patient's COM.

Figure 3:
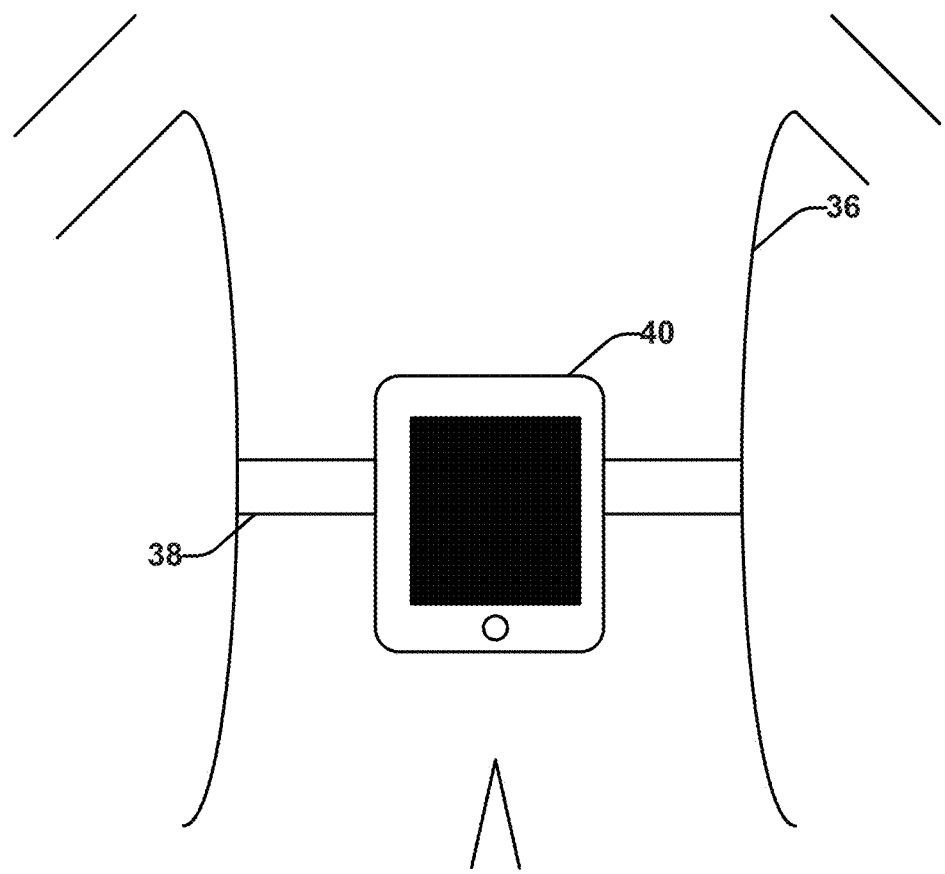
FIG. 3 depicts a schematic example of a patient wearing a portable data capture device that can be utilized to assess balance of a patient.
Figures 4A, 4B:
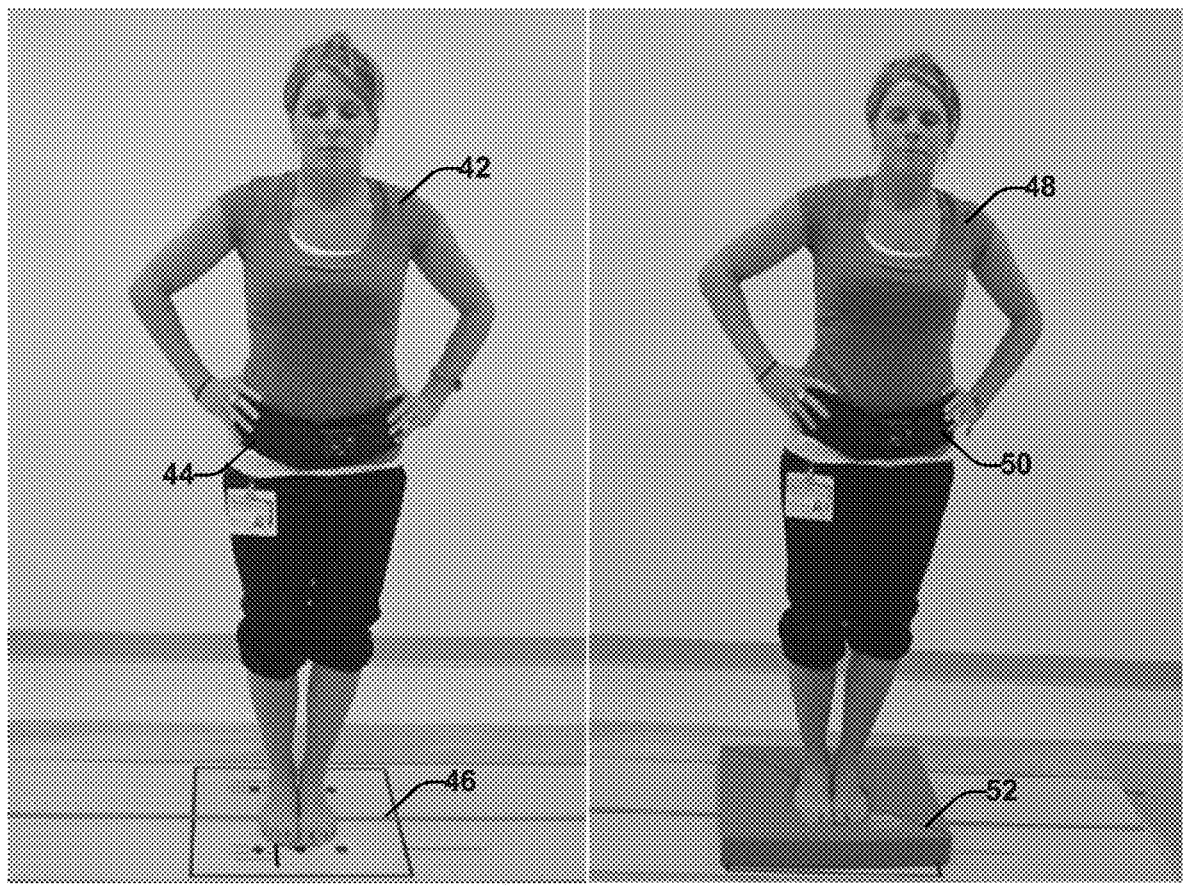
FIGS. 4A and 4B depict examples of images showing a patient performing a test that can be used to assess balance of a patient with a portable data capture device attached to the patient.

An example of such attachment is shown schematically in FIG. 3. A portable device 40 can be attached to a patient 36 at a desired position by an attachment mechanism 38. In some examples, the desired position for the portable device 40 can be on the backside of the torso of the patient 36 in proximity to the COM. The positioning of the portable device 40 with a determined spatial relationship to the COM of the patient 36 can enable the test data acquired by the sensor within the tablet computer (e.g., an accelerometer and a gyrometer operable to detect motion and/or inertia in three dimensions) to be transformed to the motion and/or inertia of the patient's COM. As illustrated, the portable device 40 is a tablet computer attached to the patient 36 by the attachment mechanism 38. However, the portable device is not limited to a tablet computer. FIG. 4 depicts images 4A, 4B of a patient 42, 48 undergoing a set of balance tests. Image 4A shows the patient 42 undergoing a double leg test (without a pad 46). Image 4B shows the patient 48 undergoing a double leg test on pad 52 (e.g., a soft, foam pad). The different surfaces provide differing sets of testing conditions that can be further evaluated by the testing apparatus 12 of FIG. 1. During both tests, the patient 42, 48 has a tablet computing device attached (by a strap 44, 50) to a position in proximity to the patient's COM. Sensors within the tablet computing device attached to the patient can acquire test data during the test interval of each of the double leg test and the double leg on pad test. In some examples, the tablet computer can transmit the test data to the testing apparatus 12 of FIG. 1 for processing. In other examples, the testing apparatus 12 of FIG. 1 can be integrated in the tablet computer and thus be configured to perform the processing. In other examples, the tablet computer can be configured to execute at least a portion of the processing of testing apparatus 12 of FIG. 1 and a second machine (e.g., another computing device) can perform the rest of the processing.

Figure 5A:
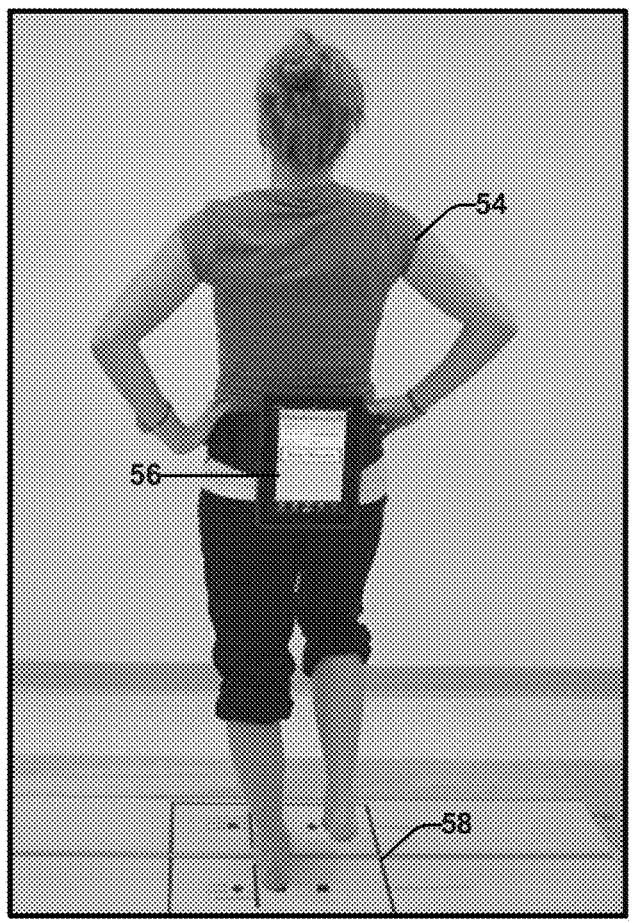
FIGS. 5A and 5B depict examples of images showing a patient performing another test that can be used to assess balance of a patient with a portable data capture device attached to the patient.
Figure 5B:
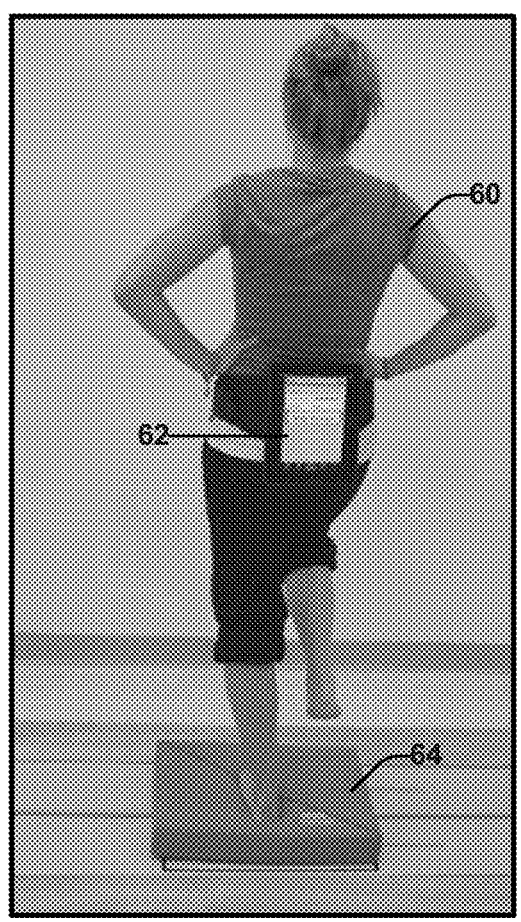

FIG. 5 depicts images 5A, 5B of a patient 54, 60 undergoing another set of balance tests. Image 5A shows the patient 54 undergoing a single leg test (without a pad 58). Image 5B shows the patient 60 undergoing a single leg test on pad 64 (e.g., a soft, foam pad). The different surfaces provide differing sets of testing conditions that can be further evaluated by the testing apparatus 12 of FIG. 1. During both tests, the patient 54, 60 has a tablet computing device 56, 62 attached (by a strap) to a position in proximity to the patient's COM. Sensors within the tablet computing device attached to the patient can acquire test data during the test interval of each of the single leg test and the single leg on pad test. In some examples, the tablet computer can transmit the test data to the testing apparatus 12 of FIG. 1 for processing. In other examples, the testing apparatus 12 of FIG. 1 can be integrated in the tablet computer and thus be configured to perform the processing. In other examples, the tablet computer can be configured to execute at least a portion of the processing of testing apparatus 12 of FIG. 1 and a second machine (e.g., another computing device) can perform the rest of the processing.

FIG. 6 depicts images 6A, 6B of a patient 66, 72 undergoing another set of balance tests. Image 6A shows the patient 66 undergoing a tandem leg test (without a pad 70). Image 6B shows the patient 72 undergoing a tandem leg test on pad 76 (e.g., a soft, foam pad). The different surfaces provide differing sets of testing conditions that can be further evaluated by the testing apparatus 12 of FIG. 1. During both tests, the patient 66, 72 has a tablet computing device attached (by a strap 68, 74) to a position in proximity to the patient's COM. Sensors within the tablet computing device attached to the patient can acquire test data during the test interval of each of the tandem leg test and the tandem leg on pad test. In some examples, the tablet computer can transmit the test data to the testing apparatus 12 of FIG. 1 for processing. In other examples, the testing apparatus 12 of FIG. 1 can be integrated in the tablet computer and thus be configured to perform the processing. In other examples, the tablet computer can be configured to execute at least a portion of the processing of testing apparatus 12 of FIG. 1 and a second machine (e.g., another computing device) can perform the rest of the processing. In still other examples, the tablet computer can be configured to collect the data and then project the data to a monitor that can provide real-time feedback of the patient's balance. This approach can be used, for example, for the training of postural stability.

The processing can be accomplished by the application programs 20 and the associated modules 22 as illustrated in FIG. 1. In either example, the test data and processed test data for a given patient can be stored in a corresponding database (e.g., a remotely located database and/or a database located within the testing apparatus).

Figure 7:
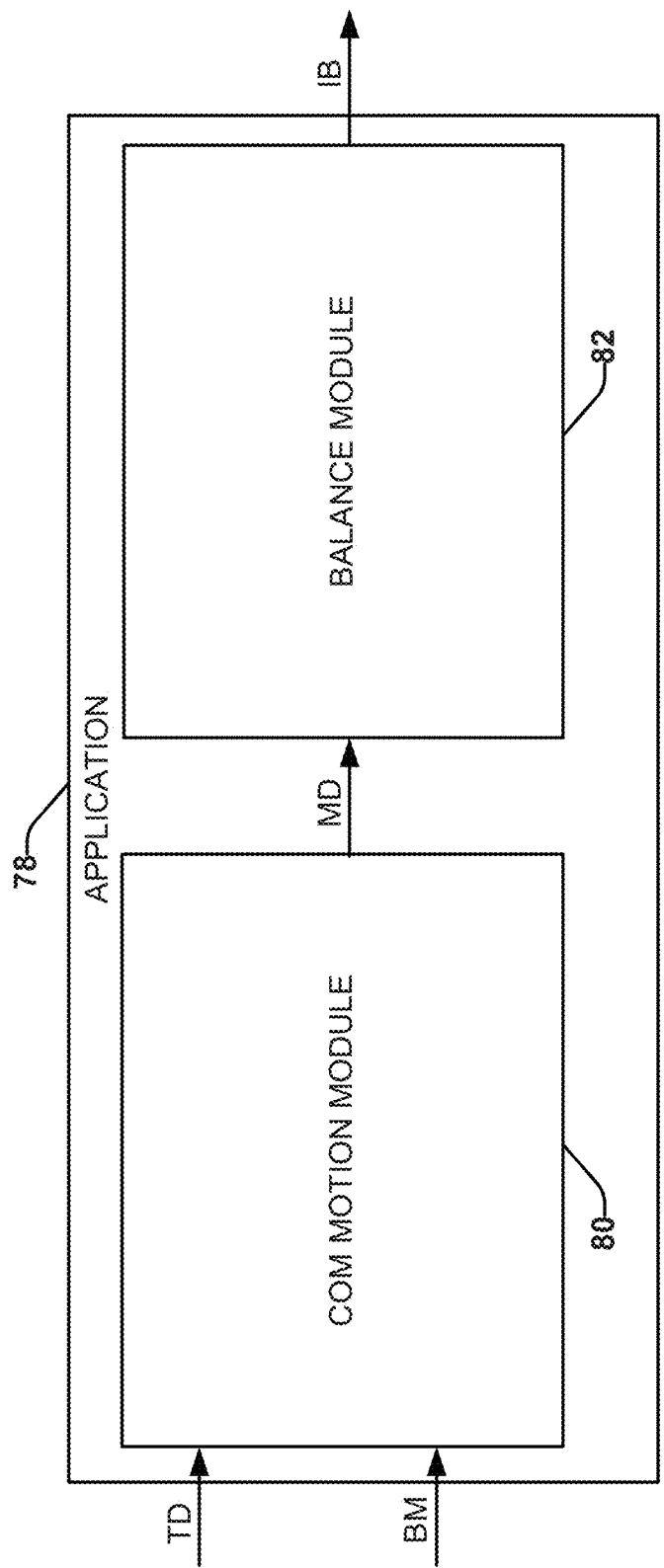
FIG. 7 depicts an example of a block diagram showing various modules of an application that can be utilized to assess balance of a patient.

FIG. 7 depicts an example application 78 (that can be an application programs 20) associated with a COM motion module 80 and a balance module 82 (that collectively can be associated modules 22).

The COM motion module 80 can receive the test data (TD) representing motion and/or inertia of a patient's COM recorded by the one or more sensors during the test interval, which can include multiple separate tests. The test data (TD) can be pre-processed before reaching the COM motion module 80 and/or within the COM motion module 80. For example, the pre-processing can process the test data to derive related processed motion data that can include acceleration data, jerk data, velocity data, rotational rate data and rotational position data for the test interval.

The COM motion module 80 can also receive a biomechanical model (BM). By way of example, the biomechanical model (BM) can be generated through statistical modeling, such as a linear mixed effects model. For example, the biomechanical model (BM) can be configured sync the test data (TD) or the processed test data with center of pressure data acquired using an accepted standard approach. This process can be repeated for a sufficient patient population and tests so that the model exhibits a sufficient confidence in converting the test data (TD) or the processed data to corresponding COM motion data (MD).

The COM motion module 80 can apply the biomechanical model (BM) to the test data (TD) or the processed data to provide COM motion data (MD) representing movement of the COM in multiple dimensions for the patient during the test interval. The COM motion data can be determined for each test (and/or each test interval) completed by the patient. Additional data can be determined based on comparative evaluations or statistical evaluations based on the COM motion data computed for each test. The balance module 82 can receive the COM motion data (MD) and determine an indication of balance for the patient based on the COM motion data (MD).

Figure 8:
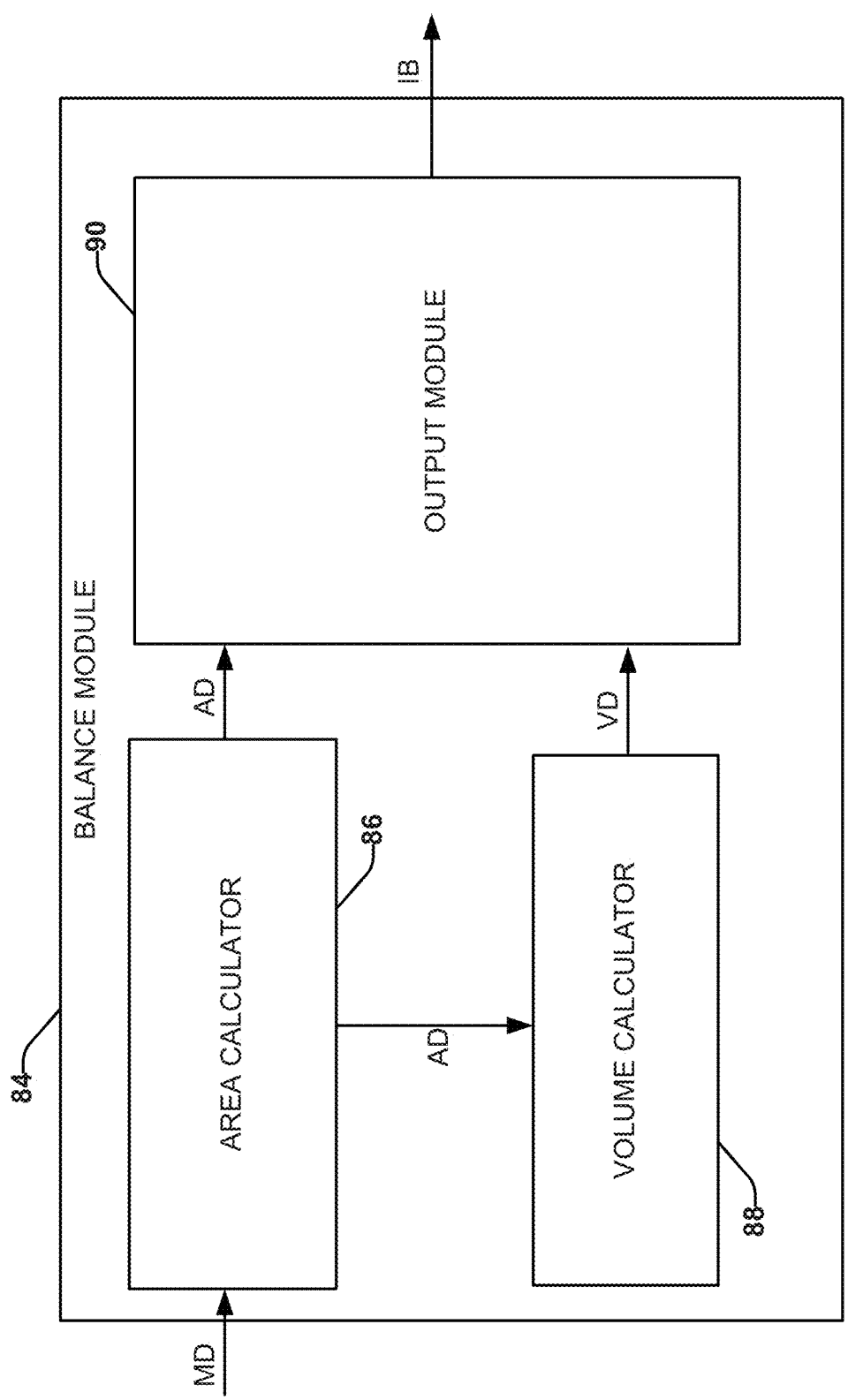
FIG. 8 depicts an example of a block diagram showing various calculators that can be a part of a balance module that can be used to assess balance of a patient.

The balance module 82 can analyze the balance and/or stability based on the COM motion data (MD) by providing an indication of balance (IB) as an output. FIG. 8 shows one example of the processing that can be undertaken by the balance module 84 to provide the indication of balance (IB). Balance module 84 can receive the COM motion data (MD) and area data (AAD) can be calculated by an area calculator 86. The area data (AAD) can correspond to the area covered by sway or motion. The area data (AAD) can be sent to an output module 90 and included in the indication of balance (IB). Additionally or alternatively, the area data (AAD) can be transmitted to a volume calculator 88 that can compute volume data (VD) related to the volume covered by the sway or motion. The volume data (VD) can be sent to the output module 90 and can be included in the indication of balance (IB).

For example, balance module 82 and/or balance module 84 can construct the output indication of balance (IB) to be displayed on a display (e.g., display 28 of FIG. 1). The display 28 can be coupled to the testing apparatus 12 to receive and display a graphical and/or text-based representation of the indication of balance. For example, the display 28 can be an interactive display, such as a touch screen. In some examples the display 28 can be connected directly to and/or be an integrated part of the testing apparatus 12. In other examples, the display 28 can be remote from the testing apparatus 12 and can be connected to the testing apparatus 12 via a communications link (e.g., a network connection), which can include physical and/or wireless connections.

The output of the indication of balance (IB) by the balance module 82, 84 can be a visualization that can be displayed on the display 28. For example, the visualization can be animated in real time during completion of one or more balance tests. As another example, the visualization can be generated based on stored data from a prior test.

Figure 9A:
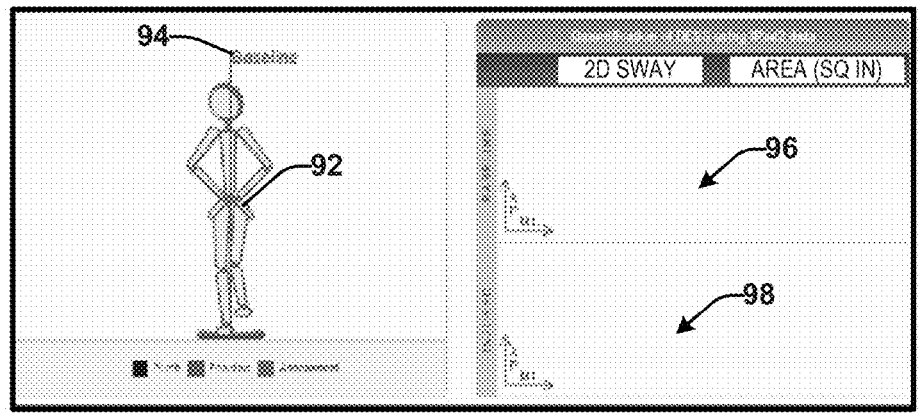
FIGS. 9A, 9B, and 9C depict examples of an output display, including an avatar, that can be generated based on data acquired for a given test.
Figure 9B:
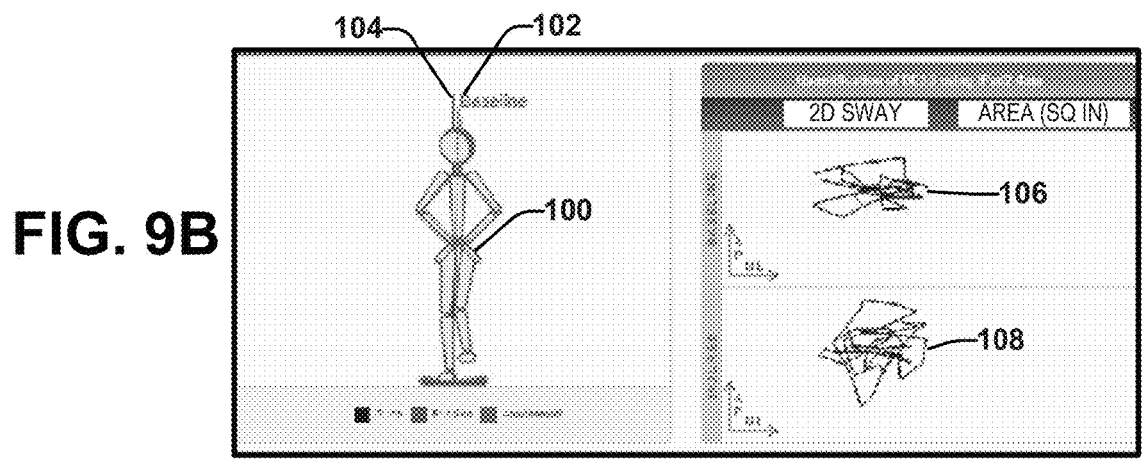
Figure 9C:
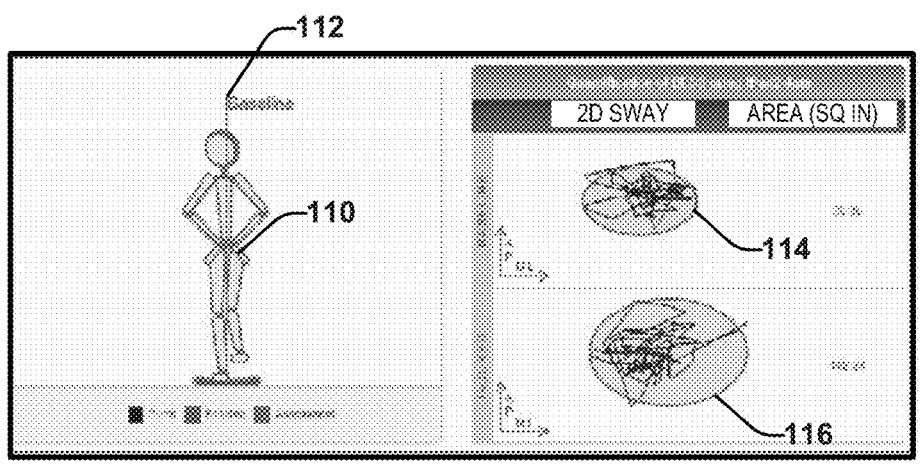
Figure 10A:
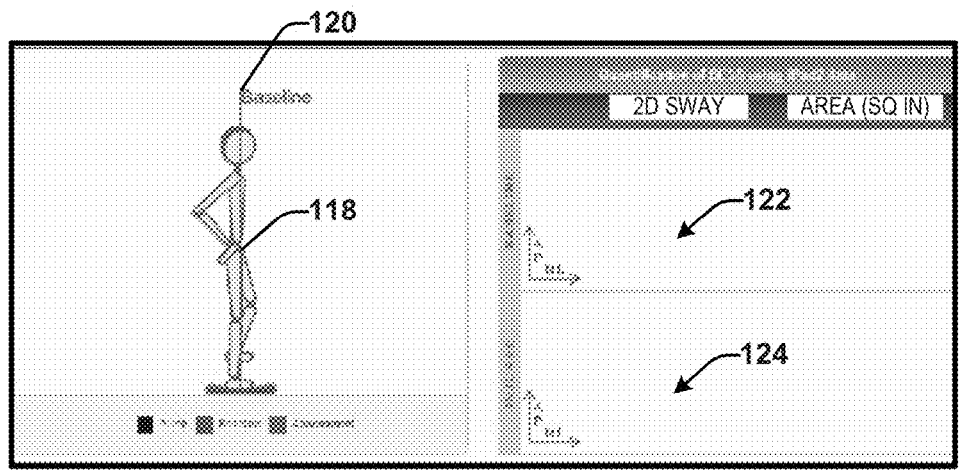
FIGS. 10A, 10B and 10C depict examples of another view of the output display that can be generated based on data acquired during the given test.
Figure 10B:
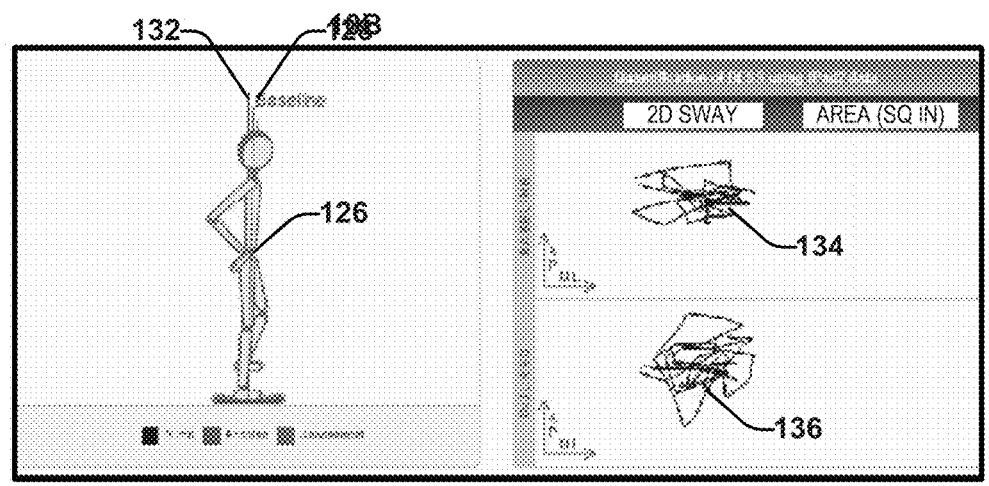
Figure 10C:
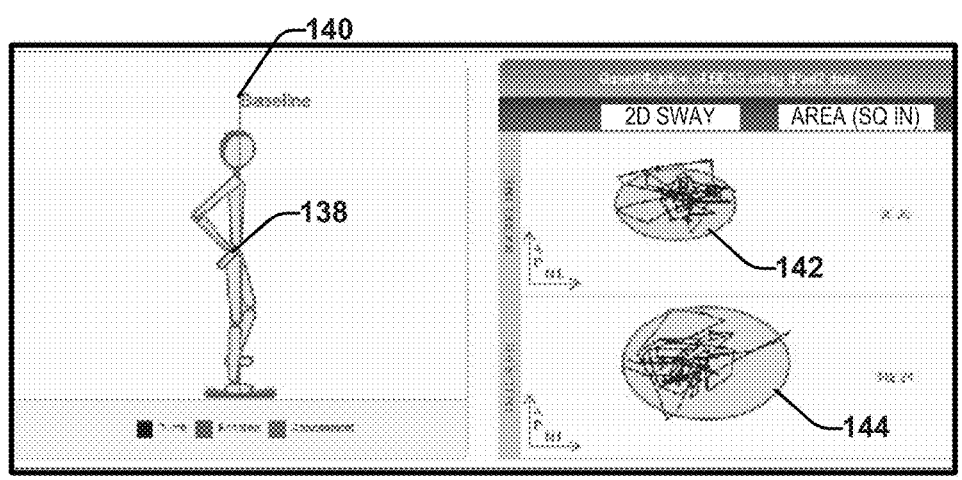
Figure 11A:
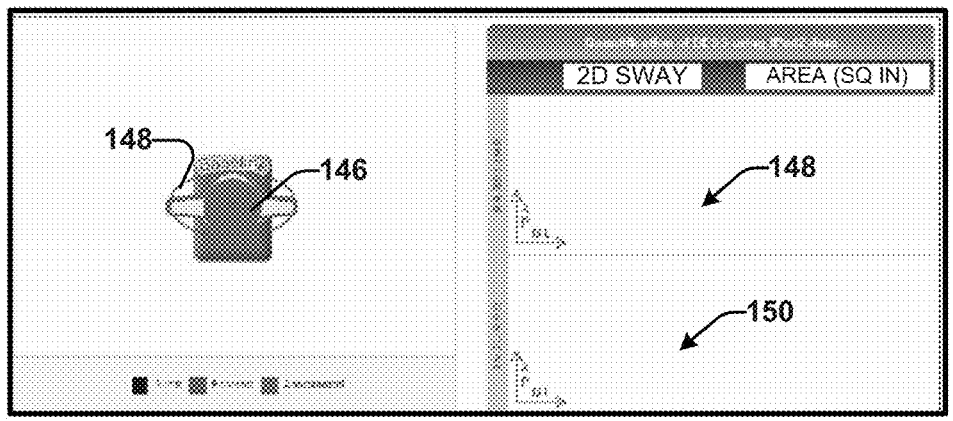
FIGS. 11A, 11B and 11C depict examples of yet another view of the output display that can be generated based on data acquired during the given test.
Figure 11B:
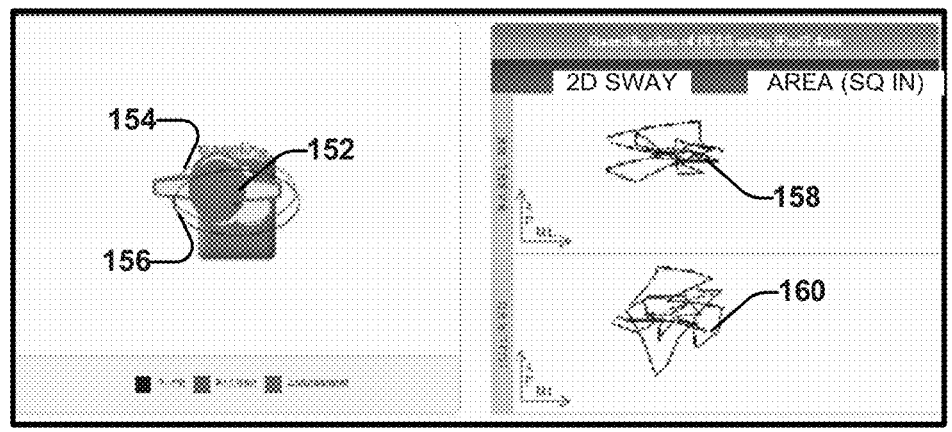
Figure 11C:
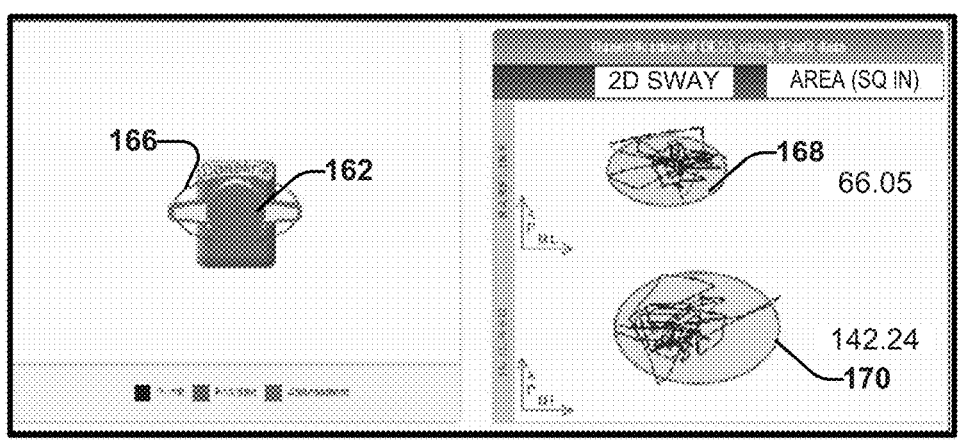
Figure 12A:
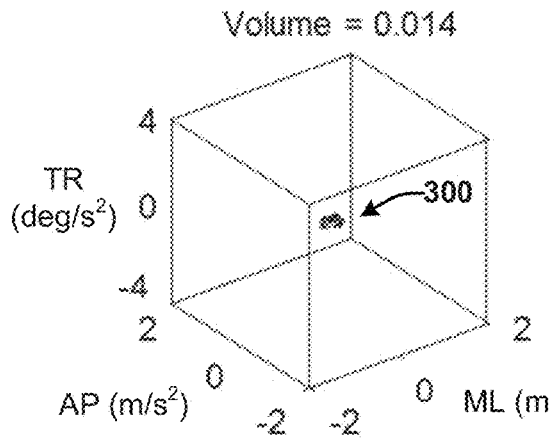
FIGS. 12A, 12B, 12C, 12D, 12E, and 12F depict examples of a 3D trace that can be part of the output display.
Figure 12B:
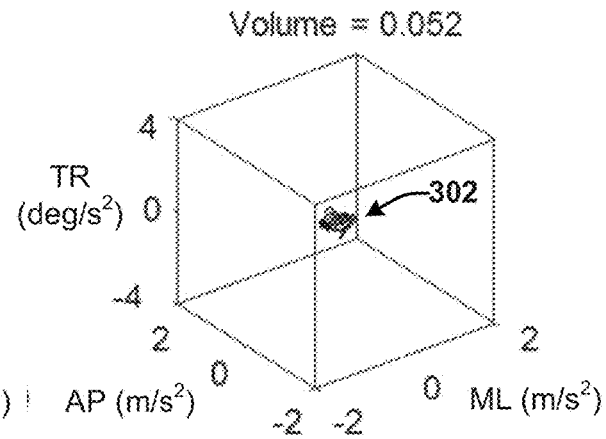
Figure 12C:
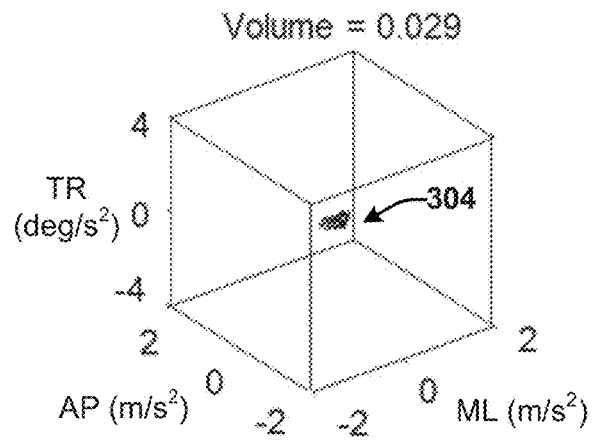
Figure 12D:
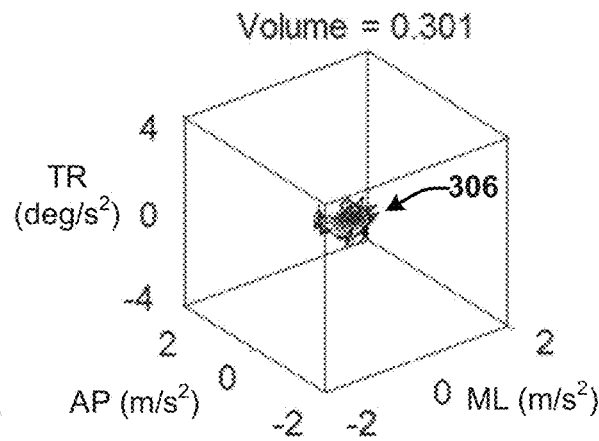
Figure 12E:
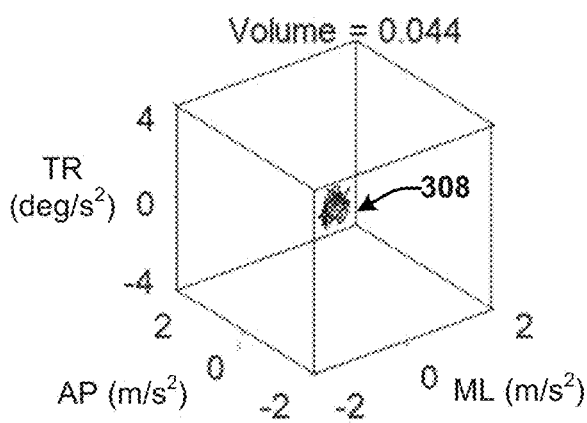
Figure 12F:
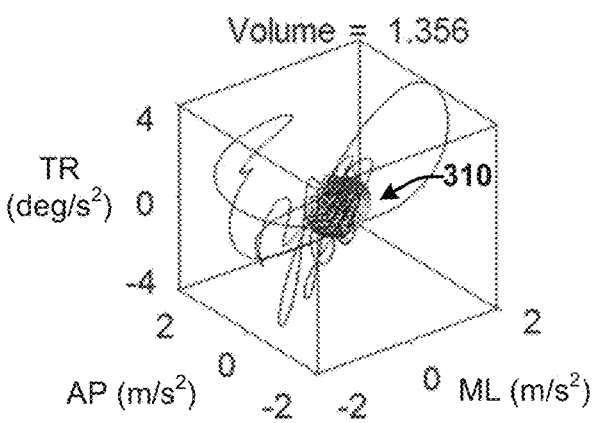

FIGS. 9, 10, and 11 depict different examples 9A-C, 10A-C, 11A-C of an output display, that includes an avatar (front view 92, 100, 110, side view 118, 126, 138, top view 146, 152, 162) of a person that can be generated based on data acquired for a given test. In some examples, the avatar can be animated in three dimensions according to the patient's movement (e.g., along the anterior-posterior direction and/or the medial-lateral direction) based on the sensor data, the processed sensor data, and/or the COM motion data. The avatar can be displayed with a baseline reference 94, 102, 112, 120, 128, 140, 148, 154, 166 that can allow a user to visually see how the patient's balance motion compares to the baseline reference. In some examples, the avatar can be superimposed on the baseline reference.

For example, the baseline reference can be established based on data from one or more healthy patients (e.g., an average value of data from a plurality of healthy patients) representing hypothetical statistically normal patient. There can be a plurality of baseline references that can be selected for a given patient based on demographic information and/or disease or disorder types. For instance, a baseline reference can be selected based on demographic information such as patient age, patient gender, patient weight, patient height, and/or patient fitness level. The demographic information for a given patient can be entered by a user or obtained from an EHR, for example. For example, the baseline reference for a 16 year old male football player can be based on balance data from one or more athletic males from a similar demographic group (e.g., ages 15-25). In other words, the baseline reference utilized for the 16 year old male football player can be different from the baseline reference for a 65 year old female with multiple sclerosis. That is baseline references can be selected according to demographic and disorder for each patient.

Additionally or alternatively, the animation can include a balance motion reference that has been established from the current patient's historical balanced motion data, and a plumb reference (which is directed toward the patient's distribution of weight).

In some examples, the output can include a plot of the motion of the COM based on the COM motion data. As illustrated in FIGS. 9-11, the plot can relate to the area of the baseline 96, 106, 114, 122, 134, 142, 148, 158, 168 and/or to the area of the patient's movement during the test 98, 108, 116, 124, 134, 142, 150, 160, 170. The plot is not limited to area and may, additionally or alternatively, be related to the volume of the baseline and the volume of the patient's movement. In some examples, the plot can be animated as a trace of the motion of the COM over the time interval. In some instances, the plot can be in two dimensions (area calculated based on the COM motion data). In other instances, the plot can be in three dimensions (volume calculated from the COM motion data).

In other examples, the output can additionally or alternatively include a 3-D trace combining linear and angular acceleration (e.g., based on accelerometer data and gyrometer data). Several examples of example 3-D traces 300, 302, 304, 306, 308, and 310 representing 95% volumes combining the anterior posterior (A-P) plane, the medial-lateral (M-L) plane, and the transverse-rotational (T-R) plane for six different balance conditions for a representative patient are shown in FIG. 12. Traces 300 (firm surface) and 302 (foam surface) each represent the patient's balance during a double-leg stance with eyes open. Traces 304 (firm surface) and 306 (foam surface) each represent the patient's balance during a double-leg stance with eyes closed. Traces 308 (firm surface) and 310 (foam surface) during a tandem stance with eyes open. Traces 308 and 310 show significant differences in ML and AP sway with different surfaces (firm vs. foam) when comparing tandem stances with open eyes. With different stances (double leg vs. tandem), a greater ML and AP sway is seen when comparing eyes open on a foam surface (trace 300 and trace 302).

A score can be calculated based on the area (e.g., shown in FIGS. 9-11) and/or the volume (e.g., shown in FIG. 12). For example, the score can be a function of the area and/or the volume. Additionally or alternatively, the score can be calculated based on a comparison between the patient's area and/or volume relative to a baseline area and/or baseline volume. The score can be used alone and/or in combination with the output as an indication of the patient's balance and/or neuromotor function. As an example, the score and/or the visualizations can be utilized as part of a screening process for evaluating concussion related injuries, stroke, multiple sclerosis, as well as other neurological or neuromotor conditions.

Figure 13:
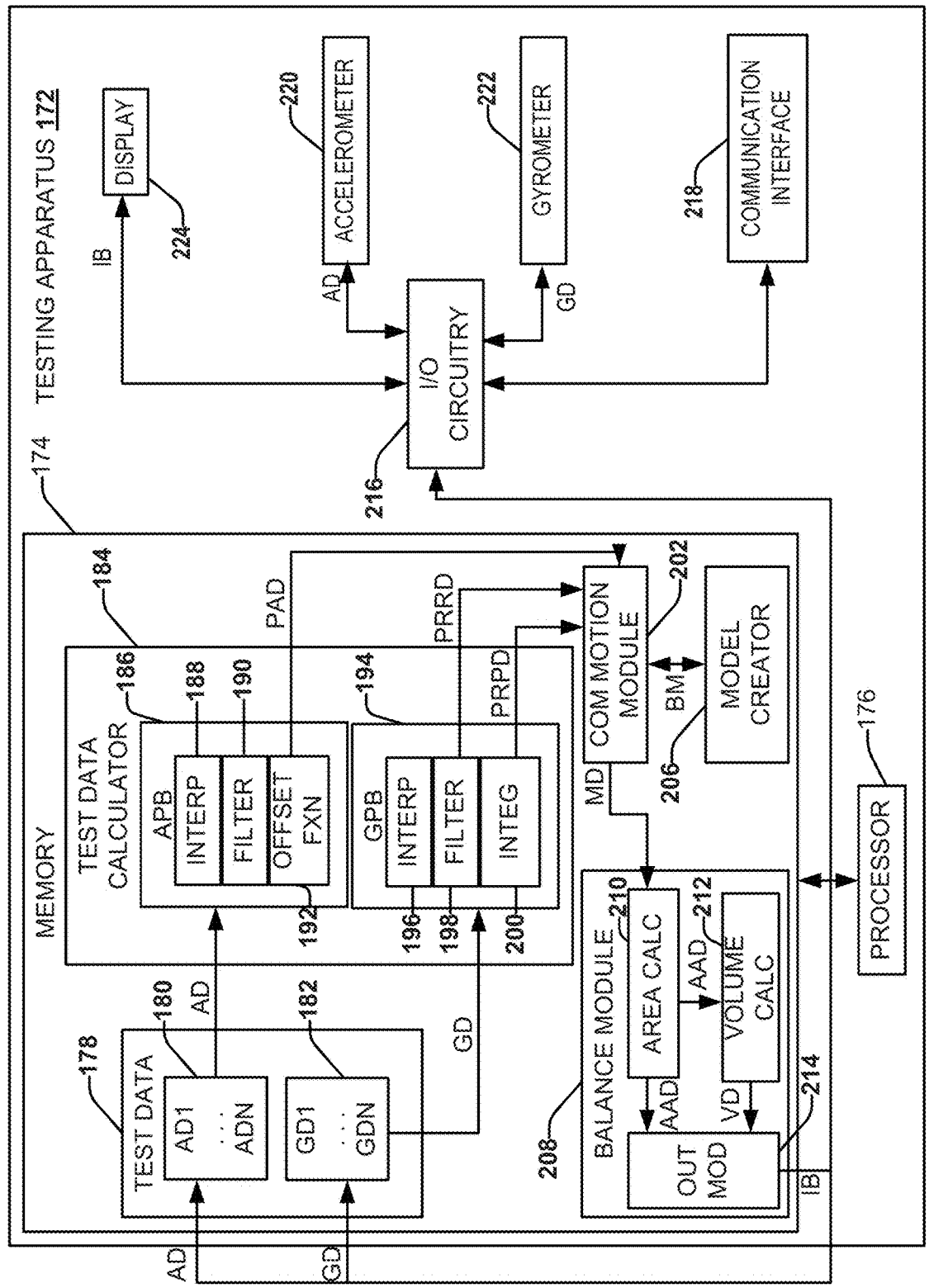
FIG. 13 depicts another example of a block diagram of a system that can be used to assess balance of a patient.

FIG. 13 depicts an example of another system (testing apparatus 172) configured to assess balance of a patient (or a plurality of patients). Similar to system 10, testing apparatus 172 includes a memory 174, a processor 176, I/O circuitry 216, communication interface 218, display 224, and sensors (accelerometer 220 and gyrometer 222). It will be appreciated that although the display 224 and the sensors (accelerometer 220 and gyrometer 222) are illustrated within the testing apparatus 172, the display 224 and/or the sensors (accelerometer 220 and gyrometer 222) can be located outside the testing apparatus 172 and communicatively coupled to the testing apparatus. It will be appreciated that similarly labeled components function similarly in system 10 and testing apparatus 172.

The testing apparatus 172 can receive accelerometer data (AD) from one or more accelerometers (e.g., accelerometer 220). Additionally or alternatively, the testing apparatus 172 can receive gyrometer data (GD) from one or more gyrometers (e.g., gyrometer 222). The accelerometer 220 and/or the gyrometer 222 can be configured to acquire data in three dimensions. The accelerometer data (AD) and the gyroscope data (GD) can be stored in the memory 174 as test data 178. The test data 178 can store a plurality of accelerometer data (AD1-ADN). Additionally or alternatively, the test data 178 can store a plurality of gyrometer data (GD1-GDN).

The test data 178 can be passed to a test data calculator 184 that is configured to pre-process the test data. The test data calculator 184 can be configured to process the test data 178 for a given test and/or a plurality of tests to prepare such data for enabling subsequent calculations and analysis.

For example, the acceleration data (AD1-AND) can be pre-processed by an accelerometer processing block (APB) 186. For example, The APB can include a variety of functions, such as an interpolation function 188, a filtering function 190, and an offset function 192. The interpolation function 188 can interpolate between dropped data points that may exist in the accelerometer data (AD1-ADN). As mentioned, the accelerometer data (AD1-ADN) can include accelerometer data along three orthogonal axes (e.g., x, y and z) to provide acceleration in three-dimensional space for the patient. Thus the interpolation function can append the accelerometer data (AD1-ADN) to include drop data points that might exist in the sample acceleration data. Such interpolation can be performed, for example, using the cubic spline or other interpolation methods. The interpolated data can then be filtered by a filtering function 190. For example, the filter function can perform low pass filtering (e.g., a Butterworth fourth order filter with a 1.25 hertz cut-off frequency) to provide filtered and interpolated data. The filtered and interpolated data can then be processed by the offset function 192 to accommodate for variances in positioning of the device relative to a patient's COM, for example. The post processed acceleration data (PAD) can then be stored in the memory 174. It will be appreciated that the APB can undertake different processing functions than the ones described. Additionally or alternatively, the gyrometer data (GD1-GDN) can be provided to a gyrometer processing block (GPB) 196 of the test data calculator 184. The GPB 194 can include a variety of functions, such as an interpolation function 196, a filtering function 198, and an integration function 200. The interpolation function 196 and the filtering function 198 can be similar to and/or the same as that implemented in the APB 186. The GPB 194 can perform interpolation and low pass filtering to provide processed rotational rate data (PRRD) based on the gyrometer data (GD1-GDN). The filtered interpolated data can further be processed by the integration function 200 to provide processed rotational position data (PRPD). The processed rotational rate data (PRRD) and/or the processed rotational position data (PRPD) can then be stored in the memory 174. It will be appreciated that the GPB can undertake different processing functions than the ones described.

For example, the test data calculator 184 can provide a processed data set that includes the processed acceleration data (PAD), the processed rotational rate data (PRRD), and the processed rotational position data (PRPD) for use in analyzing balance. The processed data set can be passed to a COM motion module 202. The COM motion module 202 can also receive one or more biomechanical models (BM). Based on the biomechanical model (BM) and the processed data set, the COM motion model can determine COM motion data (MD). For example, the biomechanical model (BM) can be applied to the processed data for computing COM motion data (MD) in a plurality of orthogonal planes (e.g., the anterior posterior (A-P) and the medial-lateral (M-L) planes). The biomechanical model (BM) can be utilized to calculate a theoretical X, Y, Z position of the patient's COM in three-dimensional space based on the processed data, which can include a positional data in three-dimensional space or can include an angular calculation for every set of test data The biomechanical model (BM) can be provided to the COM motion module 202 by a model creator 206.

By way of example, the model creator 206 can generate the biomechanical model through a statistical modeling technique, such as a linear mixed effects model. For instance, the technique used to generate the data used for the statistical modeling technique can include movement data recorded from a standard approach such as, for example, the NeuroCom Sensory Organization Test (SOT), commercially available from NeuroCom of Clackamas, Oreg. In this sense, the COM motion module 202 can configure the biomechanical model (BM) to sync the COM data derived from test data 178 and/or the preprocessed data set with center of pressure data acquired using the accepted standard approach (e.g., NeuroCom SOT or other accepted approach). This process can be repeated for a sufficient patient population and tests so that the model exhibits a sufficient confidence in converting the processed data to corresponding COM motion data (MD). As a result, the biomechanical model (BM) is configured to convert the processed data set into corresponding COM motion data (MD). The biomechanical model (BM) can correspond to computing COM motion data (MD) for A-P sway and/or computing COM motion data (MD) for M-L sway. In other words, the biomechanical model (BM) can be different depending on the type of COM motion data (MD).

The biomechanical model (BM) can be generated using one or more other approaches. For example, the portable device (e.g., iPad, iPhone, iPod, other tablet computer or specially purpose sensing device) that is configured to acquire the accelerometer data (AD) and the gyrometer data (GD) can be utilized concurrently with a three-dimensional motion capture system to generate the biomechanical model (BM).

Thus, the set of processed data can represent such data relative to a coordinate system of the sensors that acquire such data. As a result, application of such data to the biomechanical model (BM) can result in COM motion data (MD) with respect to the same axes X, Y and Z with a center point coincident with the patient's center of mass. As an example, the COM motion data (MD) can thus include a representation for movement of the patient's center of mass in the A-P and M-L planes. That is, the biomechanical model (BM) can convert the processed motion data to the corresponding COM motion data (CM) for the patient for each of one or more balance tests that are performed.

The motion data (MD) can be provided to a balance module 208. The balance module 208 can include an area calculator 210 that can compute area data (AAD) in one or more planes, such as the A-P, M-L and/or T-R planes of the patient based on the COM motion data. For example, the area data (AAD) can correspond to an average area computed based upon COM motion data (MD) that is detected during a respective test interval. As disclosed herein, test data 178 can be acquired for each of a plurality of different tests, each having a respective test interval during which the time series test data is acquired by one or more sensors (e.g., accelerometer 220 and gyrometer 222). Thus, a corresponding area can be determined in each plane for each respective test.

The balance module 208 can also include a volume calculator 212. The volume calculator 212 can be configured to compute volume data (VD) based upon the area data (AD) computed based on the COM motion data (MD) in multiple respective planes. For example, the areas determined along three respective orthogonal planes (e.g., the A-P, M-L and T-R planes) can be utilized to derive the volume for each given test. Each computed area and volume provides a value that quantifies the patient's balance and/or postural stability associated with a given test. The areas and/or volumes over one or more test that can individually or in combination provide a score (e.g., an index) that provides a measure of a patient's balance and/or postural stability.

The balance module 208 can include an output module 214 that can receive the area data (AAD) and/or the volume data (VD) and compute an indication of balance (IB). The indication of balance (IB) can be output on the display 224 as previously described.

The indication of balance (IB) can be displayed relative to a baseline value. By way of example, as mentioned above, historical data corresponding to one or more "normal" subjects who have completed the one or more tests. The "normal" subjects can be grouped according to age, fitness level, weight, height, heath status, etc. When a patient with a possible neurological condition (e.g., concussion, stroke, multiple sclerosis, etc.) undergoes the balance test, the system can retrieve baseline test data corresponding to one or more subjects with a common age, fitness level, weight, height, and/or health status of the patient to create the baseline data. For example, in the case of multiple baseline data sets, the balance module 208 can create the baseline data based on an average or weighted average of the multiple baseline data sets. Accordingly, the baseline data for the healthy 16 year old male football player will be different from the baseline data for the 65 year old female with multiple sclerosis.

As another example, the baseline data can also be customized for the patient with the patient's own historical data. For example, the patient can take the balance test at a previous time (e.g., without the symptoms of the neurological disease and/or at a different stage of the neurological disease). The same tests can also be performed at another time, such as following an injury or other incident or occasion, such as for assessing a level of progress for a patient.

The system thus can include balance module 208 that can be programmed to compare the baseline data relative to test data acquired at a different time, such as associated with an incident or disorder that is being assessed by the acquired data. The balance module 208 can analyze the respective computed data (e.g., area data. volume data, COM motion data (MD), etc.). For example, the balance module 208 can compare the computed data for baseline relative to the data acquired at one or more different times.

As a further example, the balance module 208 can analyze one or more of the COM motion data (CD), the area data (AAD), and/or the volume data (VD) that have been determined for one or more different tests (e.g., a single leg test, a double leg test, tandem leg test, single leg test on pad, double leg test on pad, and tandem leg test on pad). For example, an initial baseline test can be performed as part of an initial assessment for a given patient and stored in memory as the baseline data for the patient for each test. This can include one or more different test intervals which may be aggregated together to form the baseline test data for the given patient. Following an incident or occasion for which it is desirable to determine and assess the individual's balance and stability, one or more additional tests can be performed and the corresponding COM motion data (CD), area data, and volume data can be computed as disclosed herein. The balance module 208 can utilize the area data for a given one or more of the tests to compute the 2-D ellipse or other shape to quantify a corresponding measure of balance and postural stability. In other examples, the three-dimensional volume (e.g., corresponding to a 3-D ellipsoid or other volume) can be computed and evaluated by the balance module 208 to provide a corresponding measure of balance and postural stability.

As a further example, the balance module 208 can compute a difference between the baseline test data and the follow-up assessment or incident areas data or volume data that compute a corresponding error based on such comparison. The error or difference between volumes or areas thus can be utilized to assess and quantify one of balance and postural stability for the patient. The computed data and the results of the balance analysis can also be provided to the output controls for providing a corresponding output to a display 244. The output control can control the output in response to one or more user inputs depending upon the type of output that is desired. For example, a user can select one or more viewing angles for an animated avatar that is generated to visualize COM motion for the patient based on the COM motion data (CD) determined for a given test.

Figure 14:
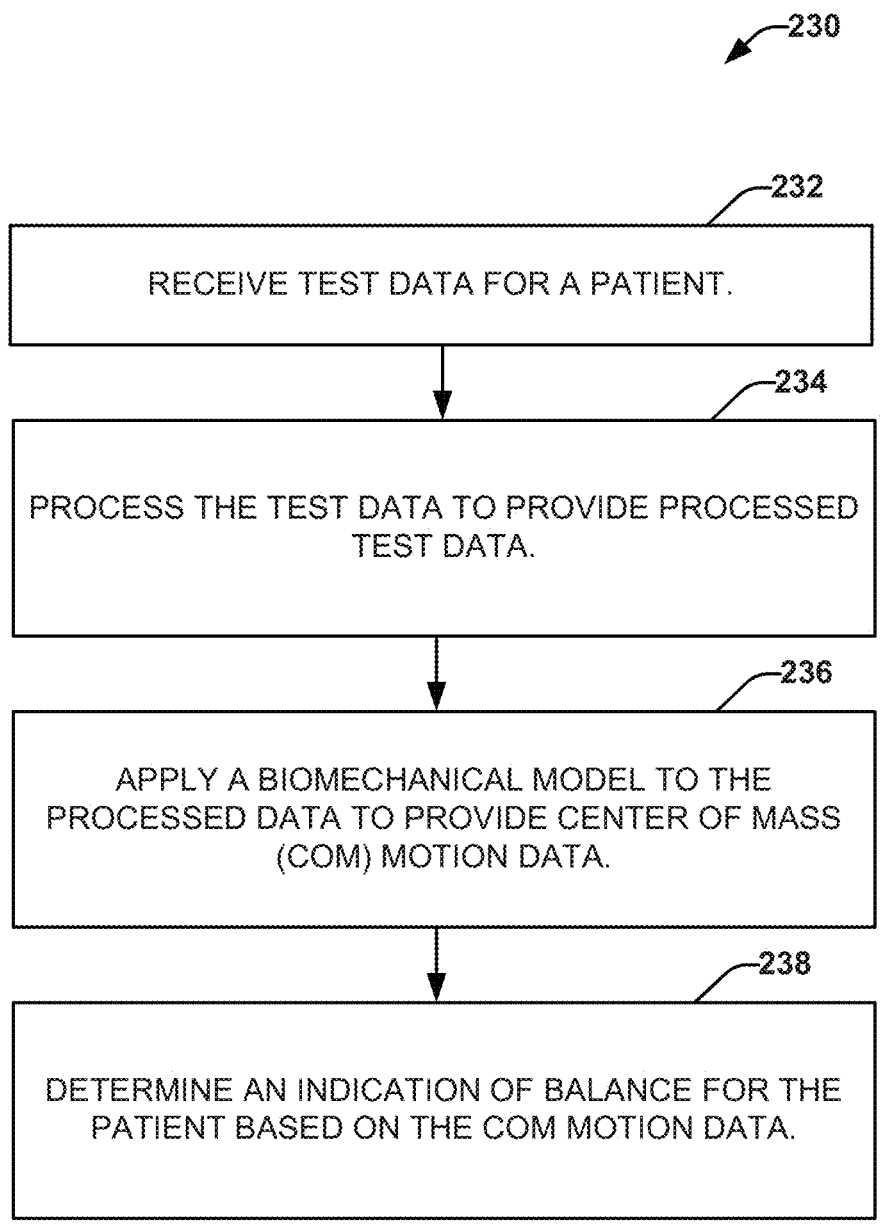
FIG. 14 depicts an example process flow diagram of a method for determining an indication of balance for a patient.
Figure 15:
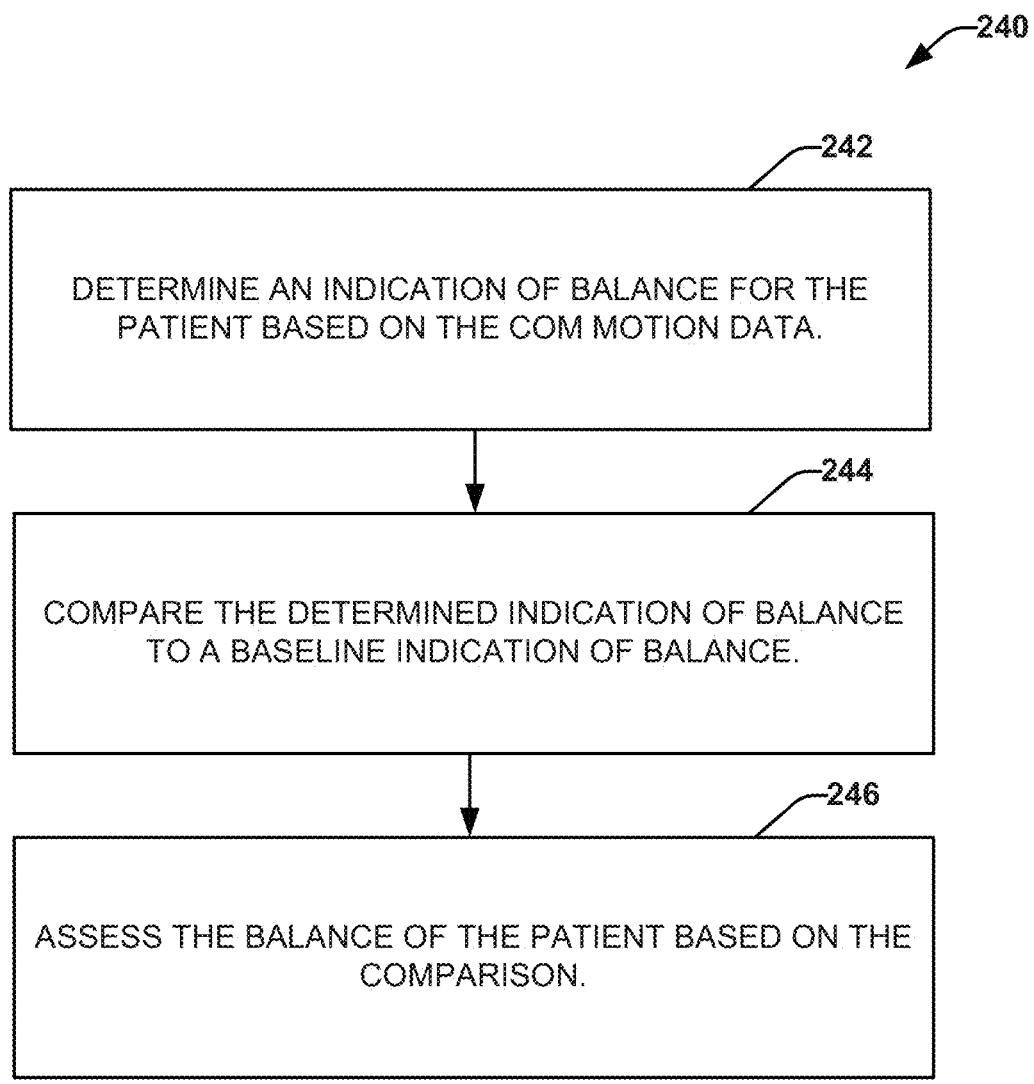
FIG. 15 depicts an example process flow diagram of a method for assessing balance of a patient.

In view of the foregoing structural and functional features described above, methods will be better appreciated with reference to FIGS. 14 and 15. While, for purposes of simplicity of explanation, the methods 230 and 240 are shown and described as executing serially, it is to be understood and appreciated that the illustrated actions, in other embodiments, may occur in different orders or concurrently with other actions. Moreover, not all illustrated features may be required to implement the methods of FIGS. 14 and 15. It is to be further understood that the following method can be implemented in hardware (e.g., in a computer or a processor based device or appliance), software (e.g., stored in a non-transitory computer readable medium or as executable instructions in memory 14 of 174, such as running on one or more processors 16 or 176), or as a combination of hardware and software.

FIG. 14 depicts a method 230 for determining an indication of balance for a patient. The method 230 can be a computer implemented method. For example, method 230 can be stored on a non-transitory computer-readable medium and executed by a processor to cause a computing device (e.g., testing apparatus 12 or 172) to perform operations of the method (as shown in acts 232-238).

At 232, test data for a patient can be received (e.g., from a sensor). The test data can represent motion of a portable device affixed to the patient during a test interval. For example, the test data can include accelerometer data and gyrometer data.

At 234, the test data can be processed to provide processed data. The processed data can include acceleration data, rotational rate data and rotational position data for the test interval. At 236, a biomechanical model can be applied to the processed data to provide COM motion data. The COM motion data can represent movement of the COM in multiple dimensions for the patient during the test interval. At 238, an indication of balance for the patient can be determined based on the COM motion data. The indication of balance can be related to a display of features related to the COM motion data (e.g., area or volume).

FIG. 15 depicts a method 240 for assessing balance of a patient. The method 240 can be a computer implemented method. For example, method 240 can be stored on a non-transitory computer-readable medium and executed by a processor to cause a computing device (e.g., testing apparatus 12 or 172) to perform operations of the method (as shown in acts 242-246).

At 242, an indication of balance can be determined for the patient based on the COM motion data. The indication of balance can be related to a display of features related to the COM motion data (e.g., area or volume). At 244, the determined indication of balance can be compared to a baseline indication of balance for the patient. The baseline indication of balance can be based on previous data for the patient and/or historical data of one or more "normal" subjects with one or more characteristics (e.g., age, health status, gender, physical fitness, height, weight, etc.) similar to the patient. For example, the baseline data can be stored in memory, and created for the patient from a plurality of stored baseline data. At 246, the balance of the patient can be assessed based on the comparison. The assessment can relate to a diagnosis of a neurological and/or a neurological or neuromotor condition.

As can be appreciated by those skilled in the art, portions of the invention may be embodied as a method, data processing system, or computer program product (e.g., a non-transitory computer readable medium having instructions executable by a processor). Accordingly, these portions of the invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable non-transitory computer-readable medium may be utilized including, but not limited to, static and dynamic storage devices, hard disks, optical storage devices, and magnetic storage devices.

Certain embodiments are disclosed herein with reference to flowchart illustrations of methods, systems, and computer program products. It can be understood that blocks of the illustrations, and combinations of blocks in the illustrations, can be implemented by computer-executable instructions. These computer-executable instructions may be provided to one or more processor cores of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in a non-transitory computer-readable medium that can direct a computer or other programmable data processing apparatus (e.g., one or more processing core) to function in a particular manner, such that the instructions stored in the computer-readable medium result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks or the associated description.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method, comprising:
    attaching a portable computing device to a patient's back proximal to a center of mass (COM) of the patient, wherein the portable computing device comprises an accelerometer and a gyrometer;
    executing, by a processor of the portable computing device, a balance test module, wherein the balance test module comprises a balance test, the executing comprises:
        acquiring test data for the patient from the accelerometer and gyrometer indicating movement of the portable computing device during performance of the balance test, wherein the test data represents motion of the portable computing device affixed to the patient during the balance test, wherein the accelerometer and the gyrometer are configured to sense the test data;
        processing the test data to provide processed data that includes at least one of acceleration data, rotational rate data and rotational position data corresponding to movement of the portable computing device during the balance test;
        applying a biomechanical model to the processed data to provide COM motion data representing movement of the COM in multiple dimensions for the patient during the at least one test;
    providing, by a processor of the portable computing device, feedback about the patient, the providing comprises:
        generating, by the processor of the portable computing device, an output related to motion of the COM of the patient based on the COM motion data; and
        displaying, by a display device, a visualization of the output on a display, wherein the visualization comprises an animated graphic that demonstrates the patient's movement along at least one axis based on the COM motion data and superimposed over a line based on the COM motion data and a baseline line that is based on reference COM motion data representing a hypothetical statistical normal patient.

2. The method of claim 1, wherein the processing the test data further comprises:
    interpolating the accelerometer data;
    filtering the interpolated acceleration data;
    applying an offset function to the filtered accelerometer data and the interpolated accelerometer data to provide acceleration data, the offset function accommodating for variations in positioning of the portable device relative to the COM of the patient;

interpolating the gyrometer data;
filtering the interpolated gyrometer data to provide rotation rate data; and
integrating the rotation rate data to provide rotational position data.

3. The method of claim 1, further comprising computing area data based on the COM motion data,
wherein the area data corresponds to a two-dimensional projection of a spatial path traveled by the COM of the patient.

4. The method of claim 3, wherein the computing the area data further comprises computing the areas in at least two orthogonal planes.

5. The method of claim 1, wherein the output comprises a graph that represents motion of the COM of the patient in a plane.

6. The method of claim 1, wherein the animated graphic further comprises an animated avatar representing the patient and demonstrating the patient's movement.

7. The method of claim 1 wherein the visualization further comprises a graphic related to a baseline motion of a COM of a population along at least one axis.

8. The method of claim 1, wherein the visualization further comprises a graphic related to a previous motion of the COM of the patient along at least one axis.

9. The method of claim 1, further comprising integrating, by the processor of the portable computing device, the output with an Electronic Health Record associated with the patient.

10. The method of claim 1, further comprising determining at least one of a motion of the patient or a balance of the patient based on the COM motion data.

11. The method of claim 1, further comprising comparing the output to a stored previous output, an output corresponding to a normal patient, or an output corresponding to a similar patient.

12. The method of claim 1, further comprising displaying a second visualization side-by-side with the visualization, wherein the second visualization comprises the area of the patient's movement during the test compared to the area of the baseline.

* * * * *

UNITED STATES PATENT AND TRADEMARK OFFICE
CERTIFICATE OF CORRECTION

PATENT NO. : 10,588,546 B2
APPLICATION NO. : 14/316217
DATED : March 17, 2020
INVENTOR(S) : David D. Schindler, Jay L. Alberts and Joshua R. Hirsch Page 1 of 1

It is certified that error appears in the above-identified patent and that said Letters Patent is hereby corrected as shown below:

In the Specification

Please replace the paragraph in Column 1, after Line 15 with the following:
--GOVERNMENT FUNDING
This invention was made was government support under NS073717 awarded by the National Institutes of Health. The government has certain rights in this invention.--

Signed and Sealed this
Sixteenth Day of June, 2020

Andrei Iancu
*Director of the United States Patent and Trademark Office*